(12) United States Patent
Matthis et al.

(10) Patent No.: US 9,119,674 B2
(45) Date of Patent: Sep. 1, 2015

(54) BONE ANCHORING DEVICE

(75) Inventors: Wilfried Matthis, Weisweil (DE); Lutz Biedermann, VS-Villingen (DE)

(73) Assignee: Biedermann Technologies GmbH & Co. KG, Donaueschigen (DE)

( * ) Notice: Subject to any disclaimer, the term of this patent is extended or adjusted under 35 U.S.C. 154(b) by 943 days.

(21) Appl. No.: 11/944,167

(22) Filed: Nov. 21, 2007

(65) Prior Publication Data

US 2008/0132957 A1   Jun. 5, 2008

Related U.S. Application Data

(60) Provisional application No. 60/860,958, filed on Nov. 22, 2006.

(30) Foreign Application Priority Data

Nov. 22, 2006   (EP) .................................... 06024232

(51) Int. Cl.
*A61B 17/70*   (2006.01)
*A61B 17/86*   (2006.01)

(52) U.S. Cl.
CPC ......... *A61B 17/7037* (2013.01); *A61B 17/7032* (2013.01); *A61B 17/8685* (2013.01); *A61B 17/864* (2013.01); *A61B 17/8605* (2013.01); *A61B 17/8645* (2013.01)

(58) Field of Classification Search
CPC ........... A61B 17/7001; A61B 17/7032; A61B 17/7034; A61B 17/7035; A61B 17/7037; A61B 17/7038; A61B 17/7041; A61B 17/7043; A61B 7/7046; A61B 17/8605; A61B 17/8685

USPC ........................ 606/60, 264–279, 300–320
See application file for complete search history.

(56) References Cited

U.S. PATENT DOCUMENTS

| | | | |
|---|---|---|---|
| 5,242,443 A * | 9/1993 | Kambin | 606/60 |
| 5,501,684 A | 3/1996 | Schlapfer et al. | |
| 6,113,601 A * | 9/2000 | Tatar | 606/266 |

(Continued)

FOREIGN PATENT DOCUMENTS

| | | |
|---|---|---|
| WO | WO 94/00066 | 1/1994 |
| WO | WO 01/49191 A1 | 7/2001 |
| WO | WO 2006/065607 A1 | 6/2006 |

OTHER PUBLICATIONS

European Search Report dated Apr. 20, 2007 for European Application No. 06024232.8, Mailed May 3, 2007, Biedermann Motech GmbH (9 pp.).

*Primary Examiner* — Pedro Philogene
*Assistant Examiner* — Lynnsy Summitt
(74) *Attorney, Agent, or Firm* — Christie, Parker & Hale, LLP

(57) ABSTRACT

A bone anchoring device includes a shank to be anchored in a bone or vertebra, a head, and a receiving part receiving the head for connecting the shank to a rod. The shank and the head are separate parts. The head has a bore with a cylindrical inner surface, a ring-shaped groove provided on the inner surface, and at least one slit extending from the inner surface to the outer surface of the head. The shank has a first portion for anchoring in the bone or vertebra and a second portion with a cylindrical outer surface adjoining a free end. A projection is provided on the cylindrical outer surface which engages with the ring-shaped groove of the head, when the cylindrical second portion of the shank is inserted in the bore of the head.

41 Claims, 11 Drawing Sheets

(56) References Cited

U.S. PATENT DOCUMENTS

| | | | |
|---|---|---|---|
| 6,835,196 B2* | 12/2004 | Biedermann et al. | 606/308 |
| 2002/0143341 A1* | 10/2002 | Biedermann et al. | 606/73 |
| 2004/0106925 A1* | 6/2004 | Culbert | 606/73 |
| 2004/0172031 A1* | 9/2004 | Rubecamp et al. | 606/73 |
| 2005/0049588 A1 | 3/2005 | Jackson | |
| 2005/0055026 A1* | 3/2005 | Biedermann et al. | 606/73 |
| 2005/0177156 A1 | 8/2005 | Timm et al. | |
| 2005/0182401 A1* | 8/2005 | Timm et al. | 606/61 |
| 2006/0036252 A1* | 2/2006 | Baynham et al. | 606/73 |
| 2007/0055240 A1* | 3/2007 | Matthis et al. | 606/61 |
| 2007/0118117 A1* | 5/2007 | Altarac et al. | 606/61 |

* cited by examiner

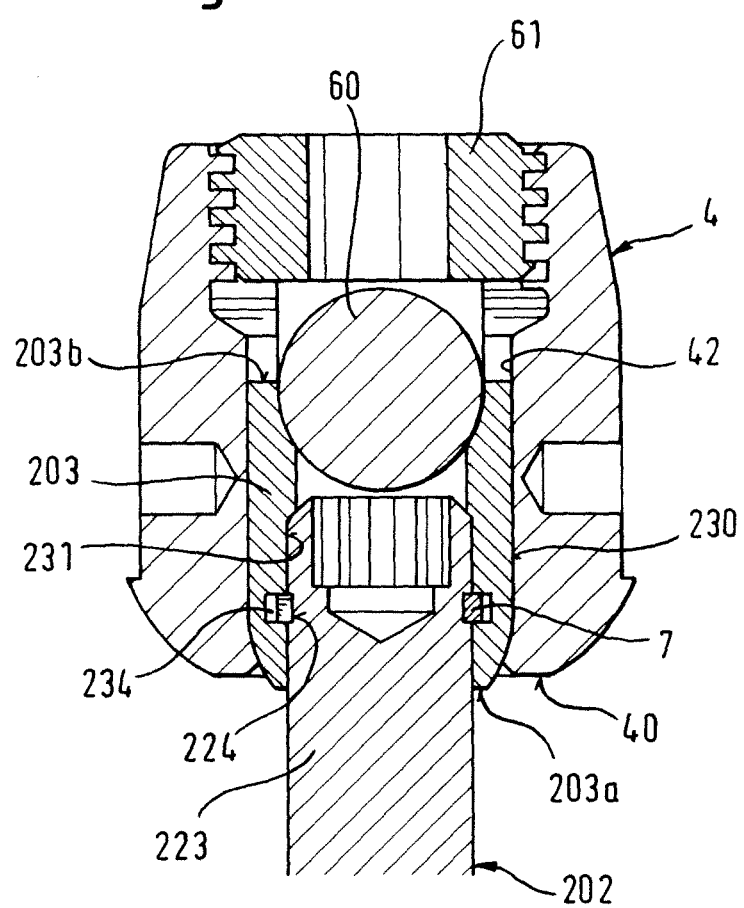

US 9,119,674 B2

BONE ANCHORING DEVICE

RELATED APPLICATIONS

The present application claims the benefit of U.S. Provisional Patent Application Ser. No. 60/860,958, filed Nov. 22, 2006, and claims priority from European Patent Application EP06024232.8, filed Nov. 22, 2006, the disclosures of which are incorporated herein by reference.

BACKGROUND

The present invention relates to a bone anchoring device, and more particularly to a polyaxial bone anchoring device having a shank and a head formed as separate parts.

U.S. Pat. No. 6,835,196 B2 describes an anchoring element for connecting a screw to a rod. The shank of the screw and the head are formed as separate parts. The head is shaped as a segment of a sphere which is pivotably held in a receiving portion. In one example the end portion of the shank has a cylindrical shape and the head is provided with a slit and has a cylindrical bore into which the cylindrical end portion of the shank is inserted.

US 2005/0049588 A1 discloses a polyaxial bone screw for connection to a spinal fixation rod. At one end the shank of the bone screw has a frusto-conical capture structure diverging in diameter in a direction away from the threaded end of the shank. A retainer ring has a central bore with a conical shape which is compatible with the conical surface of the shank for receiving the shank. The angular orientation of the shank relative to a receiving part is fixed by the spinal fixation rod acting on an end portion of the shank.

US 2006/0036252 A1 discloses a polyaxial screw which has a threaded shaft for securing the screw to bone. One end of the shaft has a reverse tapered head tapering toward and away from the shaft from an enlarged median. A spherical shaped swivel, having an opening smaller than the median, is snapped over the head to rotatably engage the shaft.

Based on the foregoing, there is a need for a bone anchoring device with a shank and a head formed as separate parts which allows convenient and reliable handling during assembly of the shank and the head, provides secure locking of the shank in the head after assembly, and provides a modular system having variability.

SUMMARY

In accordance with aspects of the disclosure, since the shank and the head are formed as separate parts, in use of the bone anchoring device, an appropriate shank can be selected depending on the application and can be connected to the head for forming the bone anchoring device. In particular, shanks of different lengths can be provided in combination with the head such that the costs for stock keeping can be reduced.

The cylindrical shape of the end portion of the shank cooperating with the cylindrical bore in the head allows convenient and reliable insertion of the shank into the head. Easy insertion is further improved by at least one slit provided in the head which imparts a certain flexibility to the head. Engagement of a projection with a corresponding groove during assembly leads to the result that the shank is securely retained in the head in an assembled condition.

BRIEF DESCRIPTION OF THE DRAWINGS

Further features and advantages of the invention will arise from the description of embodiments with reference to the enclosed figures, of which:

FIG. 11 is a sectional view of the upper part of the third embodiment in an assembled state.

DETAILED DESCRIPTION

First Embodiment

Figure 1:
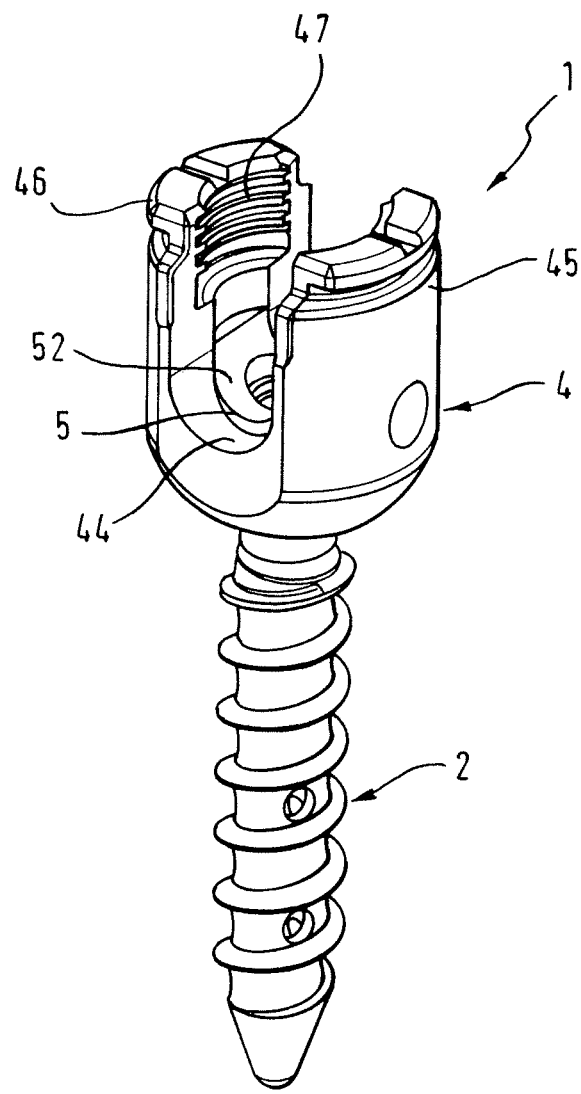
FIG. 1 is a perspective view of a bone anchoring device according to a first embodiment in an assembled condition.

A first embodiment will be described with reference to FIGS. 1 to 4. As can be seen in the exploded view of FIG. 2, the bone anchoring element 1 of the first embodiment includes a shank 2, a head 3 provided separately from the shank 2, a receiving part 4 and a pressure element 5. Further, in the first embodiment a ring 7 is provided which will be described in detail below.

As can be seen in FIG. 4a, the shank 2 comprises a tip 20, a first portion 21 which is provided with a bone thread 22, and a second portion 23 adjacent to the free end 27 opposite to the tip 20 which has a cylindrical surface. The second portion 23 has a substantially smooth surface. Further, a circumferential groove 24 is provided in the outer surface of the second portion 23. The free end 27 of the second portion 23 has a beveled shape such that the diameter tapers towards the free end 27.

Figure 3:
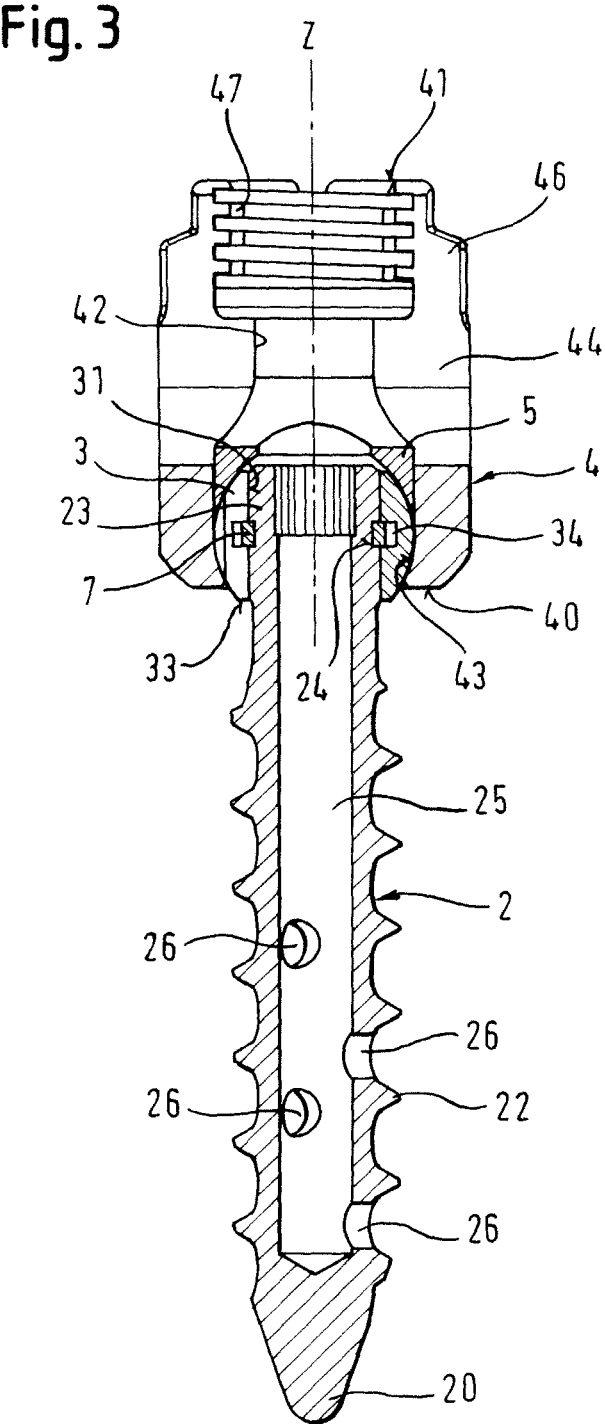
FIG. 3 is a sectional view of the bone anchoring device of FIG. 1.
Figure 4:
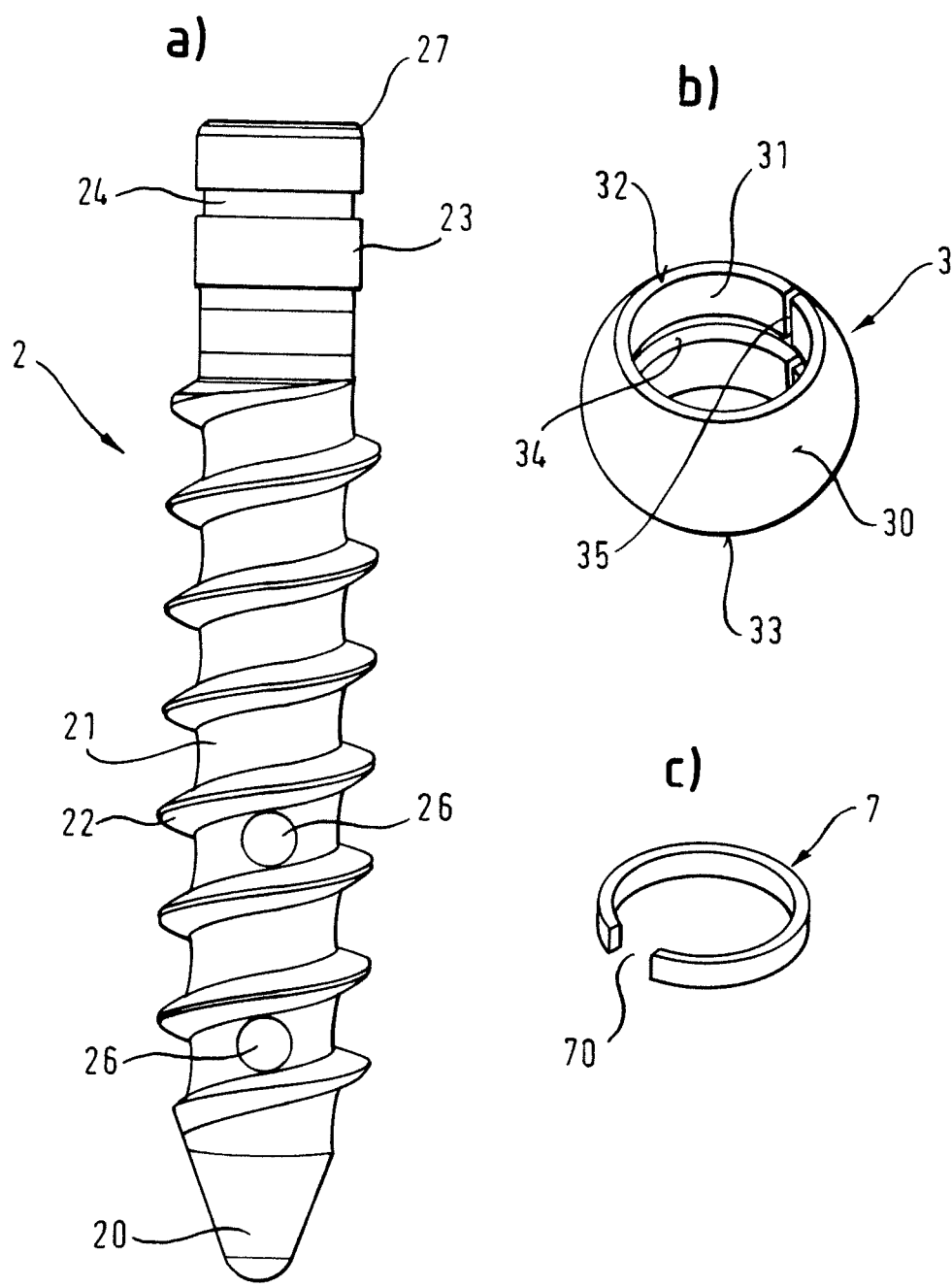
FIG. 4a to 4c are illustrations of the shank (FIG. 4a), the head (FIG. 4b), and a snap ring (FIG. 4c) of the first embodiment.

As can be seen in FIG. 3, the shank 2 is further provided with a coaxial bore 25. The bore 25 is open at the free end 27 and extends to a predetermined distance from the tip 20. Lateral through-holes 26 can be provided in the first portion 21 which extend from the bore 25 to the outer surface of the first portion. The through-holes 26 can be arranged in the base of the bone thread 22 between the thread crests. The bore 25 and the through-holes 26 allow, for example, introduction of bone cement to enhance the fixation of the shank 2 in the bone. The free end 27 of the shank further includes a recess for engagement with a screwing-in tool.

The head 3 has a substantially sleeve-like shape with a first end 32 and a second end 33. The outer surface 30 is shaped as a segment of a sphere. A cylindrical bore 31 is provided which extends through the head from the first end 32 to the second end 33. A circumferential groove 34 is provided approximately at the center of the cylindrical bore 31. As can be seen in FIGS. 3 and 4b, the groove 34 has a substantially rectangular cross section.

Further, a longitudinal slit 35 is provided in the head 3 which extends from the first end 32 to the second end 33. Although only one slit 35 which extends from the first end 32 to the second end 33 is shown in the embodiment, the slit does not have to extend continuously from the first end 32 to the second end 33. One slit extending from the first end 32 or the second end 33 to a predetermined distance from the respective other end may be provided. As an alternative, for example, several slits which alternately extend from the first end 32 to a predetermined distance from the second end 33 and from the second end 33 to a predetermined distance from the first end 32 may be provided. The slit in the head 3 serves to provide elasticity to the head 3 in order to allow insertion of a slightly oversized shank, as will be described below, and to provide secure clamping after final locking with a securing element.

The ring 7 is provided as a snap ring which has a substantially annular shape with a clearance 70, as can be seen in FIG. 4c. The ring 7 has a substantially rectangular cross section and is shaped such that it fits in the groove 24 on the second portion 23 of the shank 2 and in the groove 34 in the cylindrical bore 31 of the head 3. Due to the clearance 70 the ring 7 has certain flexibility, i.e. its diameter can be enlarged and decreased by a certain amount.

Figure 2:
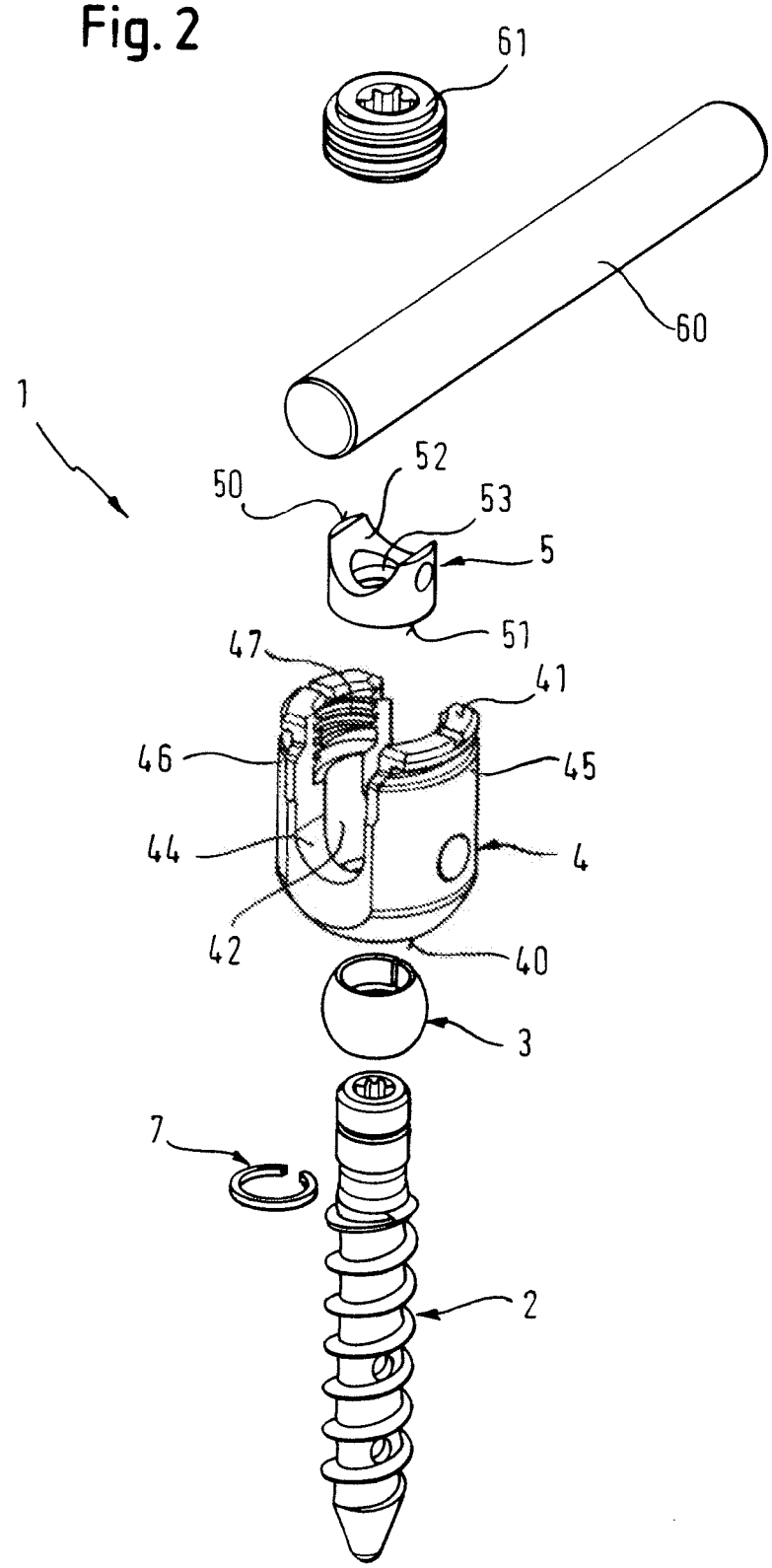
FIG. 2 is an exploded view of the bone anchoring device of FIG. 1.

As can be seen in FIGS. 2 and 3, the receiving part 4 has a substantially cylindrical shape with a first end 40 and a second end 41 and a longitudinal axis Z. A coaxial bore 42 extends through the receiving part 4 from the first end 40 to the second end 41. The shape of the longitudinal bore 42 tapers towards the first end 40 such that a seat 43 for accommodating the outer surface 30 of the head 3 is formed. The seat can have, for example, a spherical shape or a conical shape or another shape with a slightly reduced diameter of the bore, which thus provides an efficient end stop preventing the head from easily falling out off the bore. Further, a substantially U-shaped recess 44 is formed in the receiving part 4 adjacent to the second end 41 such that two free legs 45 and 46 are formed which form a channel extending substantially perpendicular to the bore 42 for receiving a rod 60. On the inner surface of the free legs 45, 46 adjacent to the second end 41 an inner thread 47 is provided for screwing-in a securing element 61 for securing the rod 60 in the U-shaped recess. In the embodiment the inner thread 47 is designed as a flat thread having the thread flanks arranged perpendicular to the longitudinal axis. However, the thread can have any other suited thread shape.

Further, as shown in FIG. 2 the pressure element 5 has a substantially cylindrical shape and is dimensioned such that it can be inserted in the coaxial bore 42 of the receiving part 4 and is slidably guided therein. On its upper side the pressure element 5 has a recess 52 shaped as a segment of a hollow cylinder the diameter of which substantially corresponds to the diameter of the bottom of the U-shaped recess 44 of the receiving part 4. On the lower side 51 of the pressure element 5 a recess (not shown) shaped as a segment of a hollow sphere is provided the diameter of which substantially corresponds to the outer diameter of the head 3. A bore 53 is provided in the pressure element 5 coaxially to its cylinder axis in order to allow guiding through of a screwing-in tool. In use, the pressure element 5 is placed in the longitudinal bore 42 such that the recess 52 shaped as a segment of a hollow cylinder is aligned with the U-shaped recess 44, as can be seen in FIG. 1.

Figure 5:
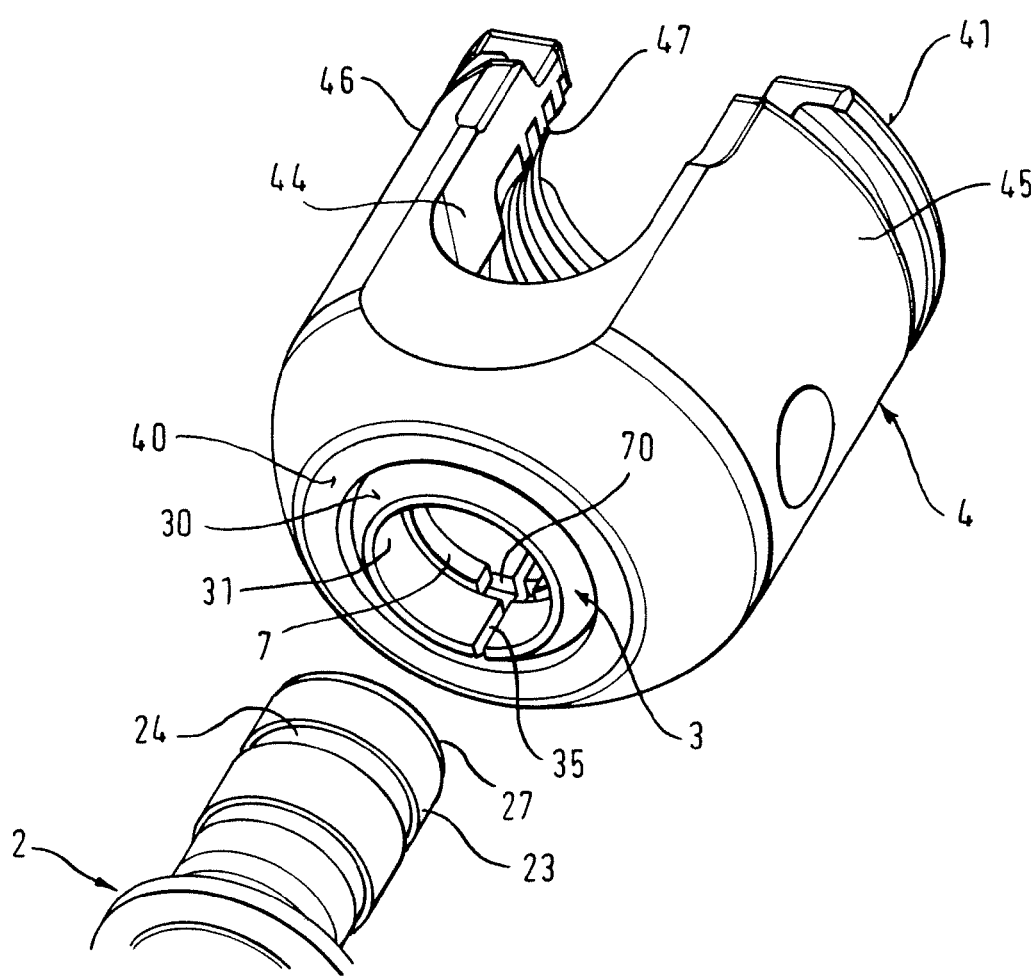
FIG. 5 is a perspective view for illustrating the assembly of the bone anchoring device according to the first embodiment.
Figure 6:
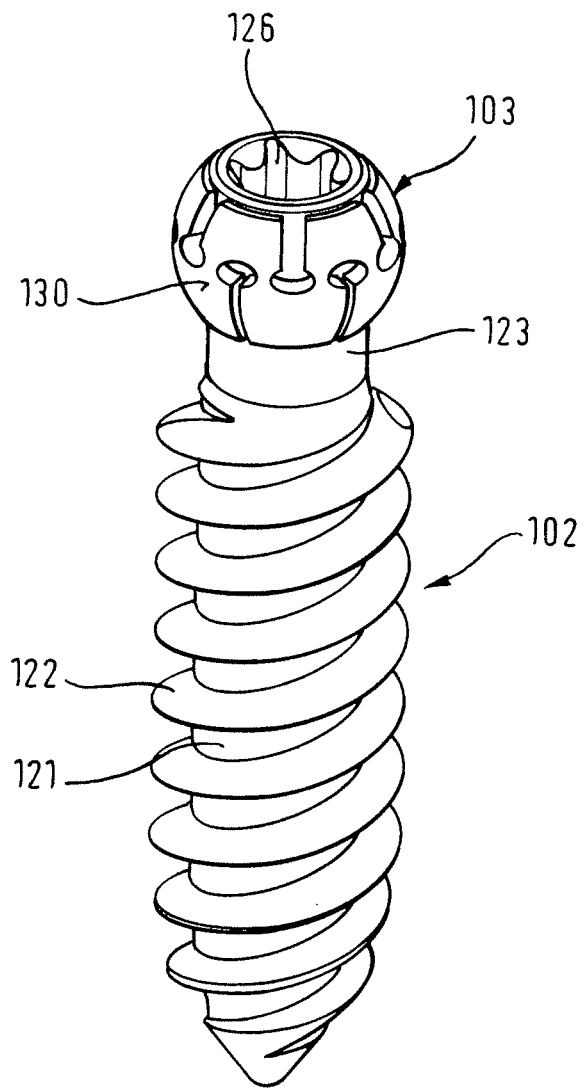
FIG. 6 is a perspective view of the shank and the head of a second embodiment.
Figure 7:
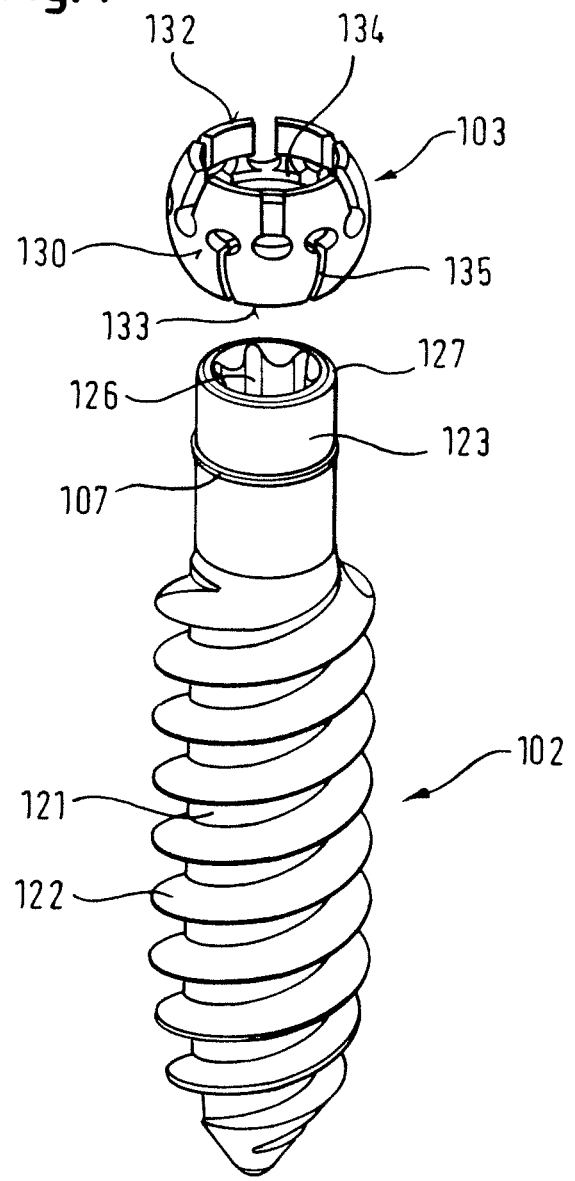
FIG. 7 is an exploded view of the embodiment of FIG. 6.

The operation of the bone anchoring device 1 of the first embodiment will now be described with reference to FIG. 5. In operation, first the shank 2 can be screwed into a bone or vertebra by engagement with a screwing-in tool. The receiving part 4, the head 3, the ring 7 and the pressure element 5 can be provided in a preassembled state. In the pre-assembled state the ring 7 is inserted in the cylindrical bore 31 of the head 3 such that it rests in the ring-shaped groove 34. Further, the head 3 is placed in the longitudinal bore 42 of the receiving part 4 such that it rests on the seat 43 and remains pivotable with respect to the receiving part 4. The pressure element 5 is placed in the longitudinal bore 42 of the receiving part 4 such that the recess on the lower side 51 faces the outer surface 30 of the head 3 and such that the recess 52 shaped as a segment of a hollow cylinder is aligned with the U-shaped recess 44. In this assembled state, due to the flexibility provided by the clearance 70, the ring 7 can still be expanded such that its diameter is enlarged. Further, due to the slit 35, the head 3 can still be expanded such that its diameter is enlarged.

The assembly of receiving part 4, head 3, ring 7 and pressure element 5 can then be connected to the shank 2 by guiding the second portion 23 of the shank 2 into the cylindrical bore 31 of the head 3. The beveled shape of the upper free end 27 of the shank 2 facilitates insertion. During insertion the head 3 and the ring 7 are slightly expanded by the second portion 23 of the shank until the ring 7 snaps into the groove 24 of the second portion 23 of the shank. In this condition the ring 7 rests in the groove 24 of the end portion of the shank 2 and in the groove 34 of the head 3. As a result, the shank 2 is prevented from retracting again from the head 3 by form-locking engagement of the ring 7 in the groove 34 in the head 3.

The cylindrical shape of the second portion 23 of the shank 2 allows easy and convenient insertion of the shank 2 into the head 3, the projection formed by the ring 7 arranged in the groove 24 on the shank 2 allows secure fixation of the shank 2 to the head 3 by form-locking.

After insertion of the shank 2 in the head 3, the angular orientation of the shank 2 relative to the cylinder axis Z of the receiving part 4 can still be varied. In operation then a rod can be placed in the U-shaped recess 44 such that it rests in the recess 52 shaped as a segment of a hollow cylinder of the pressure element 5. A securing element can be screwed-in between the legs 45, 46 by cooperating with the inner thread 47. The securing element exerts pressure on the rod and the rod in turn exerts pressure on the pressure element 5. As a result, the pressure element 5 presses on the head 3 and the angular orientation of the head 3 relative to the receiving part 4 is thereby fixed. Further, since the head 3 is pressed against the seat 43 which is formed in a tapered shape, the head 3 is slightly compressed and the connection of the shank 2 to the head 3 is further strengthened.

The slit in the head 3 provides certain elasticity to the head 3, thus, a shank 2 having a slightly over-dimensioned second portion 23 can be connected to the head 3. Further, this elasticity provides secure clamping of the shank 2 in the head 3, when the securing element is fastened.

As described above, the shank 2 is first screwed into the bone or vertebra before connecting it to the head 3. Alternatively, the shank 2 can first be connected to the head 3 and the receiving part, such that the anchoring element is in a pre-assembled state, and thereafter the shank 2 can be screwed into the bone or vertebra by guiding a screwing-in tool through the longitudinal bore 42 of the receiving part 4 and through the bore 53 of the pressure element 5 into the structure in the longitudinal bore 25 of the shank 2. Thus, variability is ensured.

Second Embodiment

A second embodiment will be described with reference to FIGS. 6 to 9. The second embodiment differs from the first embodiment in the structure of the shank and the head. The receiving part 4 and the pressure element 5 are identical to those of the first embodiment and will not be described again. The receiving part 4 and the pressure element 5 are omitted in FIGS. 6 to 9.

Figure 8:
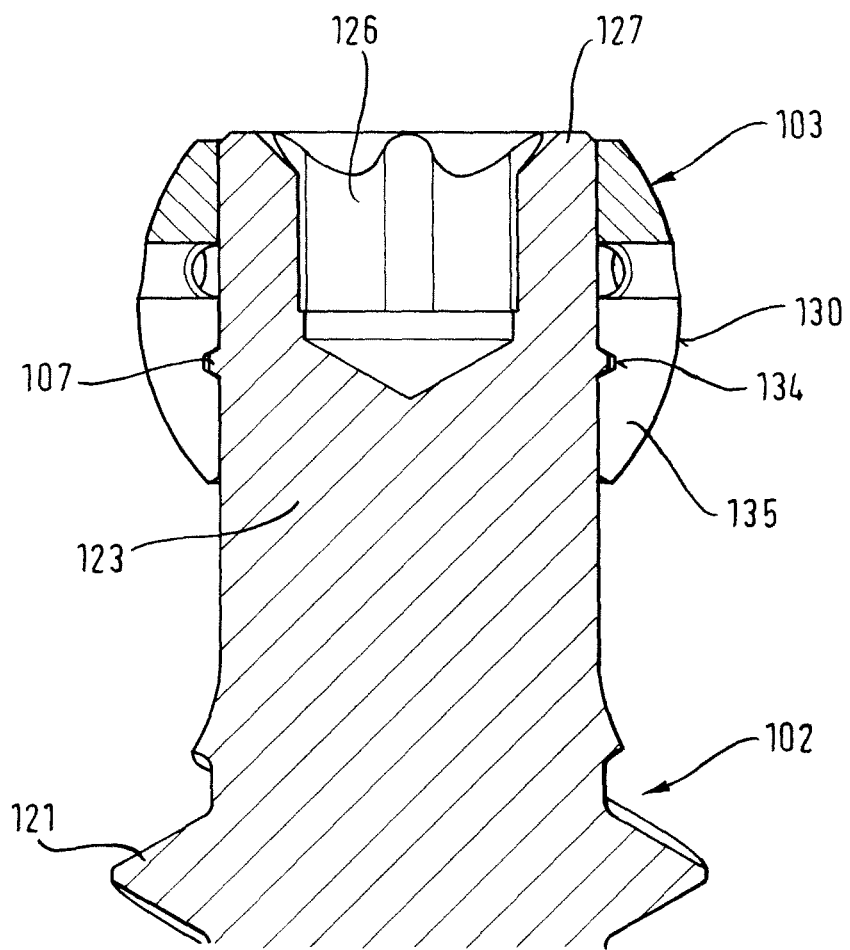
FIG. 8 is a sectional view of the upper part of the embodiment shown in FIG. 6 in an assembled state.
Figure 9:
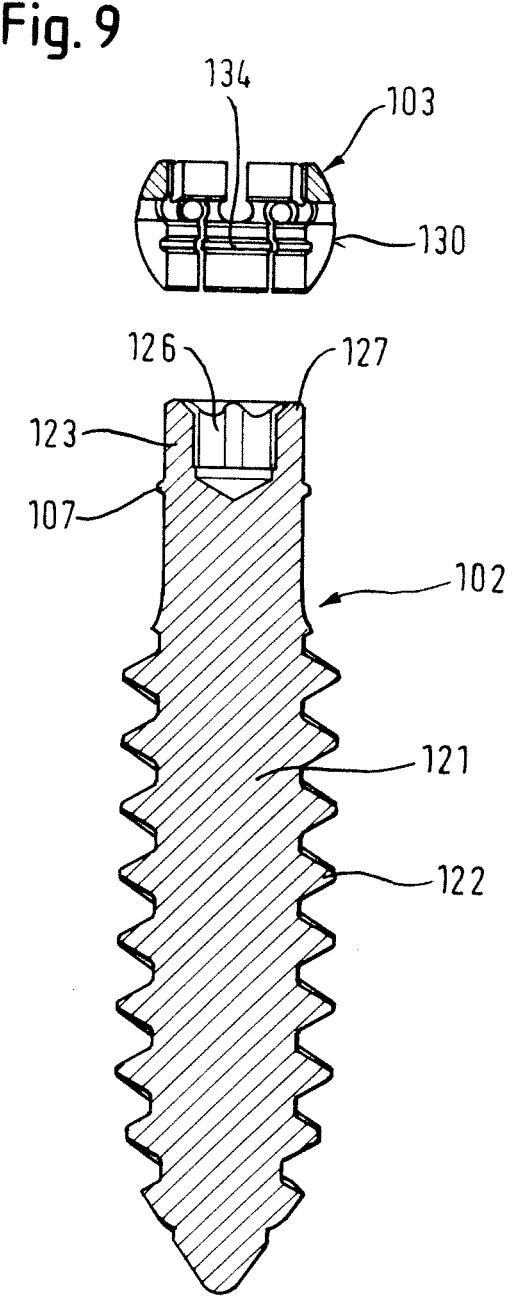
FIG. 9 is an exploded sectional view of the shank and the head of the second embodiment.

The shank 102 according to the second embodiment comprises a first portion 121 which is provided with a bone thread 122 and a second portion 123 having a cylindrical outer surface with a first diameter wherein the surface is substantially smooth. As can be seen in FIGS. 8 and 9, the shank 102 does not have a longitudinal bore as the shank in the first embodiment. A recess 126 for engagement with a screwing-in tool is provided at the free end 127. As in the first embodiment the free end 127 of the shank 102 has a beveled shape to facilitate insertion of the shank 102 into the head 103.

A circumferentially extending projection 107 is formed on the second portion 123. The projection 107 is formed integrally with the second portion 123

Similar to the first embodiment, the head 103 has a substantially sleeve-like shape. The outer surface 130 is shaped as a segment of a sphere and cylindrical bore 131 is provided. A circumferential groove 134 is provided approximately at the center of the cylindrical bore 131.

Further, a plurality of longitudinal slits 135 are provided in the head 103 which alternately extend from the first end 132 to a predetermined distance from the second end 133 and from the second end 133 to a predetermined distance from the first end 132. This structure of the slits 135 provides a uniform flexibility to the head 103 in the region of the first end 132 and in the region of the second end 133.

Operation of the second embodiment is similar to the first embodiment. When the free end 127 of the shank 102 is inserted into the cylindrical bore 131 of the head 103, the diameter of the head 103 becomes enlarged by introduction of the circular projection 107. When the projection 107 reaches the ring-shaped groove 134 in the cylindrical bore 131, the head 103 elastically contracts and the projection 107 rests in the groove 134 such that the shank 102 is prevented from retracting from the cylindrical bore 131. After assembly of the complete bone anchoring device the pressure transmitted via the pressure element 5 further enhances the fixation of the shank 102 in the head 103 similar to the first embodiment.

According to the first embodiment, a projection projecting from the cylindrical outer surface of the second portion 23 of the shank 2 is formed by the ring 7 which is placed in a groove 24 in the shank 2. Similarly in the second embodiment a projection projecting from the cylindrical outer surface of the second portion 123 of the shank 102 is formed by the circular projection 107 which is integrally formed with the second portion 123. In both cases, easy and convenient insertion of the shank 2, 102 into the cylindrical bore 31, 131 of the head 3, 103 is allowed due to the cylindrical shape of the outer surface of the second portion 23, 123. Further, in both cases the shank 2, 102 is secured against unintended retraction by means of the projection 7, 107 projecting from the outer surface of the second portion 23, 123 engaging with the groove 34, 134 provided in the head 3, 103. The slits 35, 135 provide flexibility to the respective head 3, 103 which further facilitates insertion.

Third Embodiment

Figure 10:
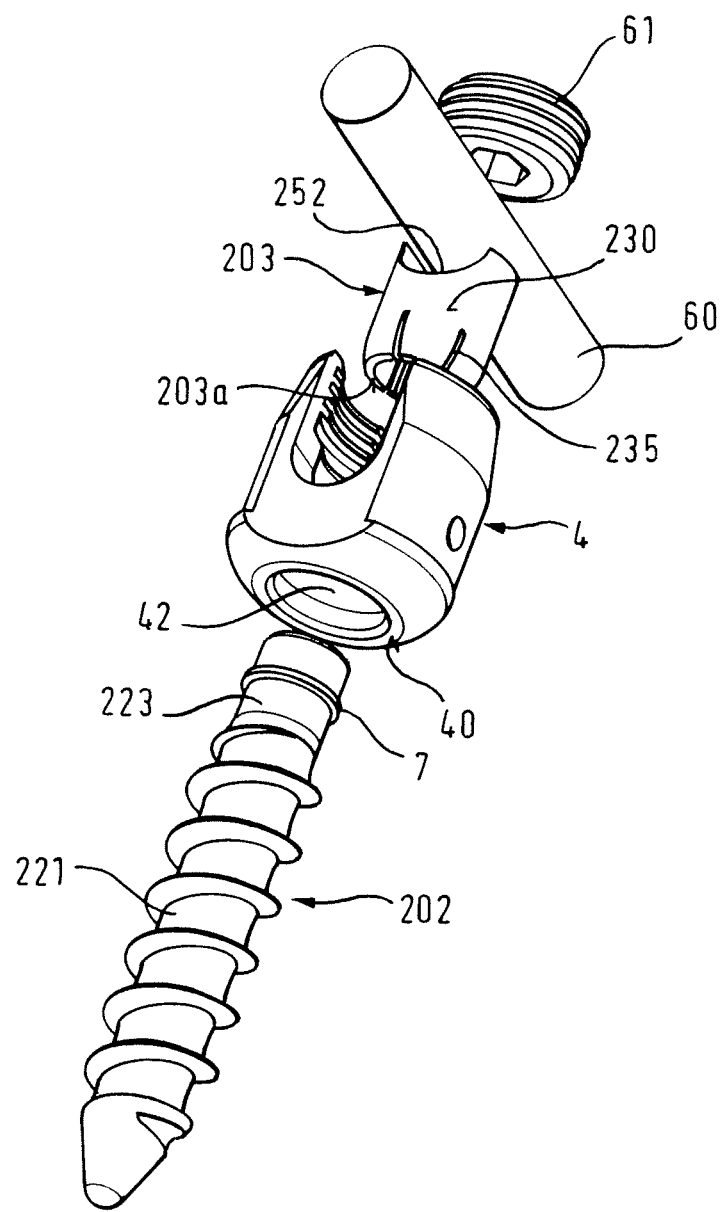
FIG. 10 is an exploded view of a third embodiment.

A third embodiment is shown in FIGS. 10 and 11. The third embodiment differs from the first and second embodiments in the structure of the head and the pressure element. The further structure is similar to that of the first and second embodiments and will not be described again.

The bone anchoring devices of the first and second embodiments provides a so-called polyaxial connection of the shank 2, 102 and the receiving part 4. In contrast, the bone anchoring device according to the third embodiment provides a monoaxial connection between a shank 202 and the receiving part 4. The shank 202 is constructed similar to the shank 2 in the first embodiment with a first portion 221, a cylindrical second portion 223 adjacent to a free end 227, and with a groove 224, but without a longitudinal bore and without through-holes.

As can be seen in FIG. 10, in the third embodiment the head and the pressure element are not constructed as separate parts but are formed in one piece as a head 203. The head 203 has a substantially cylindrical shape with a cylindrical outer surface 230 dimensioned such that it can be inserted in the longitudinal bore 42 of the receiving part 4. At a first end 203a the outer diameter of the head 203 tapers in a spherical shape. The opposite second end 203b is formed similar to the upper side 50 of the pressure element 5 in the first embodiment, i.e. a cylindrically-shaped recess 252 is formed at the second end 203b. A plurality of slits 235 extend from the first end 203a to a predetermined distance from the second end 203b. The slits 235 serve to provide flexibility to the head 203. Again, only one slit 235 may be provided alternatively.

The head 203 has a cylindrical bore 231 and a ring-shaped groove 234 similar to the head 3 in the first embodiment.

Assembly of the third embodiment is similar to the first embodiment. In operation, the head 203 is inserted in the longitudinal bore 42 of the receiving part 4. The snap ring 7 is placed in the groove 224 on the second portion 223. Then, the cylindrical second portion 223 of the shank 202 is inserted into the cylindrical bore 231 of the head 203 and the head 203 slightly widens due to the flexibility provided by the slits 235. The shank 202 is inserted until the snap ring 7 faces the ring-shaped groove 234 provided in the head 203 and then, due to the flexibility of the head 203, the snap ring 7 engages with the groove 234. As a result, the shank 202 is prevented from retracting again from the head 203.

After insertion of the rod 60 the securing element 61 is inserted for locking the rod 60 in the receiving part 4. During tightening of the securing element 61 pressure acts on the second end 203b of the head 203. The head 203 is pressed towards the first end 40 of the receiving part 4. Due to the tapering shape of the longitudinal bore 42 and to the slits 235 provided in the head 203, the head 203 is compressed and the shank 202 becomes securely locked in the head 203.

In an alternative way of operation the snap ring can first be placed in the ring-shaped groove 234 of the head 203 and thereafter the shank 202 can be inserted.

Further Modifications

In a further modification of the polyaxial bone anchoring device the shank is formed similarly to the shank 2 in the first embodiment with a groove 24 provided in the cylindrical outer surface of the second section 23. In contrast to the first embodiment the ring 7 is omitted and, instead of the ring-shaped groove 34 in the cylindrical bore 31 of the head 3, a ring-shaped projection with a reduced diameter as compared to the cylindrical bore 31 is integrally formed in the cylindrical bore 31. When the shank 2 is inserted in the cylindrical bore 31, this ring-shaped projection engages with the groove 24 of the shank 2.

As a result, a similar connection as that described with respect to the first and the second embodiments can be achieved. This structure can also be applied to the monoaxial connection shown in the third embodiment.

The ring 7 in the first and third embodiment can be considered to form a projection provided on the cylindrical inner surface of the bore 31, 231. The projection formed by the ring 7 engages with the groove 24, 224 provided on the shank 2, 202.

The structure of the projection 107 of the second embodiment cooperating with a groove provided in the head can be applied to the monoaxial connection of the third embodiment.

Although embodiments have been described in which locking of the rod and the angular orientation of the shank in the polyaxial bone anchoring device is performed by one single securing element, it is also possible to provide two securing elements for independently fixing the rod and the head. Alternatively, the securing element can be formed by an outer nut which is screwed on an outer thread provided on the free legs of the receiving part.

In the embodiments above the pressure element has a groove in the upper surface. However, it is also possible to provide a pressure element with a flat upper surface.

Further modifications are possible. For example the features of the head according to the second embodiment can be combined with the shank according to the first embodiment and vice versa.

Different types of shanks with or without coaxial bores and with different types of bone threads can be provided such that a modular system is formed. In such a system, also hooks may be provided. Further, different types of heads may be provided which can be combined with the shanks depending on the respective application. In this way, a modular system can be provided which offers variability in application.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A polyaxial bone anchoring device comprising:
a shank to be anchored in a bone or vertebra, a head, a ring, and a receiving part receiving the head for connecting the shank to a rod,
the shank, the head, and the ring being separate parts,
the head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to an outer surface of the head providing elasticity to the head;
the shank having a first portion for anchoring in the bone or vertebra and a second portion with a cylindrical outer surface, wherein a ring-shaped groove is provided on the cylindrical outer surface;
wherein the ring is configured to be arranged in the groove of the head or the shank;
wherein in a first inserted position, the ring is positioned in the grooves of the head and the shank such that a surface of the ring engages a corresponding surface on the head or the shank, the engaging surfaces configured to form a positive-locking engagement that prevents sliding between said engaging surfaces and removal of the shank from the bore of the head when a force is applied to the shank in a direction opposite a direction of insertion;
wherein the receiving part has a longitudinal bore passing through it from a first end to a second end, the longitudinal bore having a reduced diameter adjacent to the first end of the receiving part forming a seat for accommodating the head, the receiving part further having a U-shaped recess adjacent to the second end of the receiving part, the U-shaped recess intersecting the longitudinal bore such that two free legs are formed constituting a channel for receiving the rod;
wherein the shank is insertable into the head while the head is arranged in the receiving part; and
wherein a pressure element is arranged in the longitudinal bore and configured to fix the angular orientation of the shank relative to the receiving part, the pressure element acting onto the head such that it compresses the head which firmly clamps the head to the shank.

2. The polyaxial bone anchoring device according to claim 1, wherein the outer surface of the head is substantially shaped as a segment of a sphere.

3. The polyaxial bone anchoring device according to claim 1, wherein the at least one slit extends from a first end of the head to a second end of the head.

4. The polyaxial bone anchoring device according to claim 1, wherein several slits are provided in the head which alternately extend from a first end of the head to a predetermined distance from a second end of the head and from the second end of the head to a predetermined distance from the first end of the head, respectively.

5. The polyaxial bone anchoring device according to claim 1, wherein the U-shaped recess extends substantially perpendicular to the longitudinal bore.

6. The polyaxial bone anchoring device according to claim 1, wherein when the ring is provided on the inner surface of the head, the ring is configured to engage with the ring-shaped groove of the shank when the second portion of the shank is inserted in the bore of the head.

7. The polyaxial bone anchoring device according to claim 1, wherein the ring-shaped groove provided on the cylindrical inner surface is spaced apart from respective portions of the cylindrical inner surface adjacent to the first end and the second end of the head.

8. The polyaxial bone anchoring device according to claim 1, wherein the cylindrical outer surface of the second portion of the shank extends from a first end to a second end, and the ring-shaped groove provided on the cylindrical outer surface is between the first end and the second end of the cylindrical outer surface and spaced apart from the first end and the second end of the cylindrical outer surface.

9. The polyaxial bone anchoring device according to claim 1, wherein when the ring is arranged in the groove of the head, the ring is configured to expand in the head upon engagement with the shank.

10. The polyaxial bone anchoring device according to claim 1, wherein the ring comprises a snap ring having a slit.

11. The polyaxial bone anchoring device according to claim 1, wherein said engaging surface of the ring and said corresponding engaging surface on the head or the shank are matching surfaces.

12. The polyaxial bone anchoring device according to claim 1, wherein said engaging surface of the ring extends in a plane perpendicular to said direction of insertion.

13. A method of attaching a polyaxial bone anchoring device to a bone or vertebra, the polyaxial bone anchoring device comprising a shank to be anchored in a bone or vertebra, a head, a ring, and a receiving part receiving the head for connecting the shank to a rod, the shank, the head, and the ring being separate parts, the head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to an outer surface of the head providing elasticity to the head, the shank having a first portion for anchoring in the bone or vertebra and a second portion with a cylindrical outer surface, wherein a ring-shaped groove is provided on the cylindrical outer surface, wherein the ring is configured to be arranged in the groove of the head or the shank, wherein in a first inserted position, the ring is positioned in the grooves of the head and the shank such that a surface of the ring engages a corresponding surface on the head or the shank, the engaging surfaces configured to form a positive-locking engagement that prevents sliding between said engaging surfaces and removal of the shank from the bore of the head when a force is applied to the shank in a direction opposite a direction of insertion, wherein the receiving part has a longitudinal bore passing through it from a first end to a second end, the longitudinal bore having a reduced diameter adjacent to the first end of the receiving part forming a seat for accommodating the head, the receiving part further having a U-shaped recess adjacent to the second end of the receiving part, the U-shaped recess intersecting the longitudinal bore such that two free legs are formed constituting a channel for receiving the rod, wherein the shank is insertable into the head while the head is arranged in the receiving part, and wherein a pressure element is arranged in the longitudinal bore and configured to fix the angular orientation of the shank relative to the receiving part, the pressure element acting onto the head such that it compresses the head which firmly clamps the head to the shank, the method comprising:

attaching the shank to the bone or vertebra;

inserting the head in the bore of the receiving part to seat the head at the second end of the receiving part;

connecting the head to the shank by inserting the second portion of the shank in the bore of the head, wherein when the ring is provided on the inner surface of the head, the connecting of the head and the shank comprises the ring provided on the inner surface of the head engaging the ring-shaped groove on the outer surface of the shank in the first inserted position; and inserting the pressure element in the receiving part to fix the angular orientation of the shank relative to the receiving part, the pressure element acting onto the head such that it compresses the head which firmly clamps the head to the shank.

14. A polyaxial bone anchoring system comprising:

a plurality of shanks, any one of the shanks to be anchored in a bone or vertebra, at least one head, at least one ring, and a receiving part receiving the head for connecting any one of the shanks to a rod, the shanks, the head, and the ring being separate parts, the head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to an outer surface of the head providing elasticity to the head;

each shank having a first portion for anchoring in the bone or vertebra and a second portion with a cylindrical outer surface, wherein a ring-shaped groove is provided on the cylindrical outer surface;

wherein the ring is configured to be arranged in the groove of the head or one of the shanks;

wherein in a first inserted position, the ring is positioned in the grooves of the head and any one of the shanks such that a surface of the ring engages a corresponding surface on the head or the shank, the engaging surfaces configured to form a positive-locking engagement that prevents sliding between said engaging surfaces and removal of the shank from the bore of the head when a force is applied to the shank in a direction opposite a direction of insertion;

wherein the receiving part has a longitudinal bore passing through it from a first end to a second end, the longitudinal bore having a reduced diameter adjacent to the first end of the receiving part forming a seat for accommodating the head, the receiving part further having a U-shaped recess adjacent to the second end of the receiving part, the U-shaped recess intersecting the longitudinal bore such that two free legs are formed constituting a channel for receiving the rod;

wherein any one of the shanks is insertable into the head while the head is arranged in the receiving part; and wherein a pressure element is arranged in the longitudinal bore and configured to fix the angular orientation of any one of the shanks relative to the receiving part, the pressure element acting onto the head such that it compresses the head which firmly clamps the head to any one of the shanks.

15. The polyaxial bone anchoring system according to claim 14, wherein the shanks have different bone threads.

16. The polyaxial bone anchoring system according to claim 14, wherein at least one of the shanks comprises a coaxial bore and lateral through-holes extending from the bore to the outer surface of the shank.

17. The polyaxial bone anchoring system according to claim 14, further comprising a plurality of heads, each head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to the outer surface of the head providing elasticity to the head, wherein each head is connectable with any one of the shanks.

18. The polyaxial bone anchoring system according to claim 17, wherein the at least one slit of at least one of the heads extends from a first end of the head to a second end of the head.

19. The polyaxial bone anchoring system according to claim 17, wherein several slits are provided in at least one of the heads which alternately extend from a first end of the head to a predetermined distance from a second end of the head and from the second end of the head to a predetermined distance from the first end of the head, respectively.

20. The polyaxial bone anchoring system according to claim 14, wherein when the ring is provided on the inner surface of the head, the ring is configured to engage with the ring-shaped groove of any one of the shanks when the second portion of the shank is inserted in the bore of the head.

21. A bone anchoring device comprising:

a shank to be anchored in a bone or vertebra, a head, a ring, and a receiving part receiving the head for connecting the shank to a rod;

the shank, the head, and the ring being separate parts;

the head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to an outer surface of the head; and the shank having a first portion for anchoring in the bone or vertebra and a second portion with a cylindrical outer surface, the cylindrical outer surface having a ring-shaped groove;

wherein the ring is configured to be arranged in the ring-shaped groove of the head;

wherein a free end of the second portion of the shank comprises an inwardly tapered edge portion;

wherein when the ring is arranged in the groove of the head, the ring is configured to engage the free end of the shank to expand the ring by the inwardly tapered edge portion, and then to engage with the ring-shaped groove of the shank in a first inserted position, when the second portion of the shank is inserted in the bore of the head, the shank being insertable into the head while the head is arranged in the receiving part;

wherein in the first inserted position, the ring is positioned in the grooves of the head and the shank such that a surface of the ring engages a corresponding surface on the head or the shank, the engaging surfaces configured to form a positive-locking engagement that prevents sliding between said engaging surfaces and removal of the shank from the bore of the head when a force is applied to the shank in a direction opposite a direction of insertion; and wherein the receiving part has a longitudinal bore passing through it from a first end to a second end, and a U-shaped recess adjacent to the second end and intersecting the longitudinal bore such that two free legs are formed constituting a channel for receiving the rod.

22. The bone anchoring device according to claim 21, wherein the ring has a rectangular cross-sectional profile.

23. The bone anchoring device according to claim 21, wherein the outer surface of the head is substantially shaped as a segment of a sphere.

24. The bone anchoring device according to claim 21, wherein the at least one slit extends from a first end of the head to a second end of the head.

25. The bone anchoring device according to claim 21, wherein several slits are provided in the head which alternately extend from a first end of the head to a predetermined distance from a second end of the head and from the second end of the head to a predetermined distance from the first end of the head, respectively.

26. The bone anchoring device according to claim 21, wherein the longitudinal bore has a reduced diameter adjacent to the first end of the receiving part forming a seat for accommodating the head.

27. The bone anchoring device according to claim 26, wherein a pressure element is arranged in the longitudinal bore for fixing the angular orientation of the shank relative to the receiving part.

28. The bone anchoring device according to claim 26, wherein the U-shaped recess extends substantially perpendicular to the longitudinal bore.

29. The bone anchoring device according to claim 21, wherein the ring-shaped groove provided on the cylindrical inner surface is spaced apart from respective portions of the cylindrical inner surface adjacent to the first end and the second end of the head.

30. The bone anchoring device according to claim 21, wherein the cylindrical outer surface of the second portion of the shank extends from a first end to a second end, and the ring-shaped groove provided on the cylindrical outer surface is between the first end and the second end of the cylindrical outer surface and spaced apart from the first end and the second end of the cylindrical outer surface.

31. The bone anchoring device according to claim 21, wherein when the ring is arranged in the groove of the head, the ring is configured to expand in the head upon engagement with the shank.

32. The bone anchoring device according to claim 21, wherein the ring comprises a snap ring having a slit.

33. The bone anchoring device according to claim 21, wherein said engaging surface of the ring and said corresponding engaging surface on the head or the shank are matching surfaces.

34. The bone anchoring device according to claim 21, wherein said engaging surface of the ring extends in a plane perpendicular to said direction of insertion.

35. A method of attaching a bone anchoring device to a bone or vertebra, the bone anchoring device comprising a shank to be anchored in a bone or vertebra, a head, a ring, and a receiving part receiving the head for connecting the shank to a rod, the shank, the head, and the ring being separate parts, the head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to an outer surface of the head, and the shank having a first portion for anchoring in the bone or vertebra and a second portion with a cylindrical outer surface, the cylindrical outer surface having a ring-shaped groove, wherein the ring is configured to be arranged in the ring-shaped groove of the head, wherein a free end of the second portion of the shank comprises an inwardly tapered edge portion, wherein when the ring is arranged in the groove of the head, the ring is configured to engage the free end of the shank to expand the ring by the inwardly tapered edge portion, and then to engage with the ring-shaped groove of the shank in a first inserted position, when the second portion of the shank is inserted in the bore of the head, the shank being insertable into the head while the head is arranged in the receiving part, wherein in the first inserted position, the ring is positioned in the grooves of the head and the shank such that a surface of the ring engages a corresponding surface on the head or the shank, the engaging surfaces configured to form a positive-locking engagement that prevents sliding between said engaging surfaces and removal of the shank from the bore of the head when a force is applied to the shank in a direction opposite a direction of insertion, and wherein the receiving part has a longitudinal bore passing through it from a first end to a second end, and a U-shaped recess adjacent to the second end and intersecting the longitudinal bore such that two free legs are formed constituting a channel for receiving the rod, the method comprising:

attaching the shank to the bone or vertebra; and connecting the head to the shank by inserting the second portion of the shank in the bore of the head, the inserting of the second portion causing the inwardly tapered edge portion to expand at least one of the ring and the head, such that further insertion of the second portion of the shank in the bore of the head causes the ring to engage the ring-shaped groove of the shank in the first inserted position to connect the head to the shank.

36. A bone anchoring system comprising:

a plurality of shanks, any one of the shanks to be anchored in a bone or vertebra, at least one head, at least one ring, and a receiving part receiving the head for connecting any one of the shanks to a rod, the shanks, the head, and the ring being separate parts, the head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to an outer surface of the head; and each shank having a first portion for anchoring in the bone or vertebra and a second portion with a cylindrical outer surface, the cylindrical outer surface having a ring-shaped groove;

wherein the ring is configured to be arranged in the ring-shaped groove of the head;

wherein a free end of the second portion of one of the shanks comprises an inwardly tapered edge portion;

wherein when the ring is arranged in the groove of the head, the ring is configured to engage the free end of any one of the shanks to expand the ring by the inwardly tapered edge portion, and then to engage with the ring-shaped groove of the shank in a first inserted position, when the second portion of the shank is inserted in the bore of the head, the shank being insertable into the head while the head is arranged in the receiving part;

wherein in the first inserted position, the ring is positioned in the grooves of the head and the shank such that a surface of the ring engages a corresponding surface on the head or the shank, the engaging surfaces configured to form a positive-locking engagement that prevents sliding between said engaging surfaces and removal of the shank from the bore of the head when a force is applied to the shank in a direction opposite a direction of insertion; and wherein the receiving part has a longitudinal bore passing through it from a first end to a second end, and a U-shaped recess adjacent to the second end and intersecting the longitudinal bore such that two free legs are formed constituting a channel for receiving the rod.

37. The bone anchoring system according to claim 36, wherein the shanks have different bone threads.

38. The bone anchoring system according to claim 36, wherein at least one of the shanks comprises a coaxial bore and lateral through-holes extending from the bore to the outer surface of the shank.

39. The bone anchoring system according to claim 36, further comprising a plurality of heads, each head having a bore with a cylindrical inner surface defining a smallest diameter of the bore, the cylindrical inner surface extending uniformly from a first end of the head to a second end of the head and interrupted by a ring-shaped groove provided on the inner surface, and at least one slit extending from the inner surface to the outer surface of the head providing elasticity to the head, wherein each head is connectable with any one of the shanks.

40. The bone anchoring system according to claim 39, wherein the at least one slit of at least one of the heads extends from a first end of the head to a second end of the head.

41. The bone anchoring system according to claim 39, wherein several slits are provided in at least one of the heads which alternately extend from a first end of the head to a predetermined distance from a second end of the head and from the second end of the head to a predetermined distance from the first end of the head, respectively.

* * * * *

UNITED STATES PATENT AND TRADEMARK OFFICE
CERTIFICATE OF CORRECTION

| | | |
|---|---|---|
| PATENT NO. | : 9,119,674 B2 | Page 1 of 1 |
| APPLICATION NO. | : 11/944167 | |
| DATED | : September 1, 2015 | |
| INVENTOR(S) | : Wilfried Matthis et al. | |

It is certified that error appears in the above-identified patent and that said Letters Patent is hereby corrected as shown below:

On the Title Page item (73) Assignee:   Delete "Donaueschigen (DE)"

Insert -- Donaueschingen (DE) --

Signed and Sealed this
Seventh Day of June, 2016

Michelle K. Lee
*Director of the United States Patent and Trademark Office*